United States Patent [19]

Suzukamo et al.

[11] Patent Number: 4,547,586
[45] Date of Patent: Oct. 15, 1985

[54] PREPARATION OF 2-ISOPROPENYL-OR 2-ISOPROPYLIDENYL-3-HEXENOATES FROM CHRYSANTHEMIC ACID ESTERS

[75] Inventors: Gohfu Suzukamo; Mitsuhisa Tamura, both of Osaka; Masami Fukao, Shiga, all of Japan

[73] Assignee: Sumitomo Chemical Company, Limited, Osaka, Japan

[21] Appl. No.: 558,199

[22] Filed: Dec. 5, 1983

Related U.S. Application Data

[62] Division of Ser. No. 433,443, Oct. 8, 1982, Pat. No. 4,438,286.

[30] Foreign Application Priority Data

Oct. 16, 1981 [JP] Japan ................ 56-166075
Oct. 16, 1981 [JP] Japan ................ 56-166076
Oct. 16, 1981 [JP] Japan ................ 56-166077
Oct. 16, 1981 [JP] Japan ................ 56-166078
Oct. 16, 1981 [JP] Japan ................ 56-166079

[51] Int. Cl.$^4$ .......................... C07C 67/30
[52] U.S. Cl. ............................. 560/211
[58] Field of Search .................. 560/211, 205

[56] References Cited

FOREIGN PATENT DOCUMENTS 19056 11/1966 Japan .

OTHER PUBLICATIONS

Matsui, Masanao et al. Agr. Biol. Chem. vol. 29 (1965) pp. 784–786.

*Primary Examiner*—Natalie Trousof
*Assistant Examiner*—L. Hendriksen
*Attorney, Agent, or Firm*—Cushman, Darby & Cushman

[57] ABSTRACT

A novel substituted diene alcohol represented by a general formula:

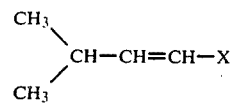

wherein X represents a group of the formula

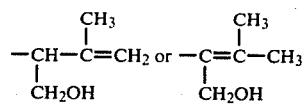

and a process for the preparation thereof a lower alkoxycarbonyl group of a substituted diene carboxylic acid ester having an E configuration obtained by the treatment of a chrysanthemic acid ester with Brönsted acid or a substituted diene carboxylic acid ester having a Z configuration obtained by the thermal cleavage of a chrysanthemic acid ester is reduced to methylol derivative.

10 Claims, No Drawings

PREPARATION OF 2-ISOPROPENYL-OR 2-ISOPROPYLIDENYL-3-HEXENOATES FROM CHRYSANTHEMIC ACID ESTERS

This is a division of application Ser. No. 433,443, filed Oct. 8, 1982, now U.S. Pat. No. 4,438,286.

The present invention provides a novel substituted diene alcohol represented by the formula (III):

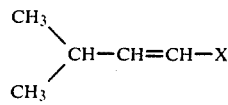

wherein X represents a group of the formula

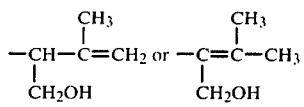

which has an E configuration when X represents a group of the formula

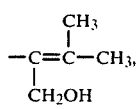

and a process for the preparation thereof, which process comprises reducing a substituted diene carboxylic acid ester having an E configuration of the formula (II-a):

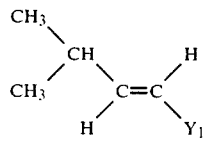

wherein Y₁ represents a group of the formula

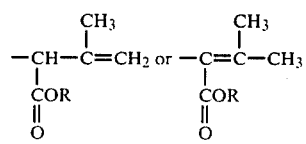

wherein R represents a lower alkyl group, which is obtained by the treatment of a chrysanthemic acid ester represented by the formula (I):

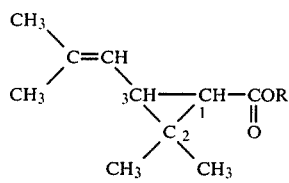

wherein R represents the same as that mentioned above with sulfonic acid or sulfuric acid, or a substituted diene carboxylic acid ester having a Z configuration represented by the general formula (II-b):

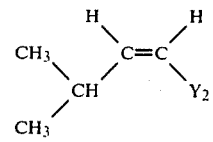

wherein Y₂ represents a group of the formula

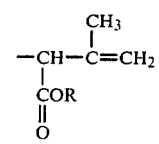

wherein R represents the same as mentioned above which is obtained by the thermal cleavage of a chrysanthemic acid ester represented by the general formula (I).

The substituted diene alcohol represented by the general formula (III) has by itself a floral note and it is useful as a perfume. Also it can be led, by the reduction, to tetrahydrolavendulol which produces rose-like perfume, which is useful as fragrants, and it is an important compound as an intermediate to prepare the same. Further, it is a useful compound as an intermediate for the preparation of pharmaceuticals and agricultural chemicals.

As a method for the preparation of substituted diene carboxylic acid esters of the general formulas (II-a) and (II-b) which are intermediates for the production of the substituted diene alcohols of the general formula (III), the following methods have been known as mentioned below.

For instance, there is reported a method wherein a substituted diene carboxylic acid ethyl ester is obtained by heating chrysanthemic acid ethyl ester at a high temperature (500° C.) [Tetrahedron Letters, 3795 (1965)]. According to said literature, the configuration related to the double bond of the product is regarded to be an E-form one. However, according to the investigation of the present inventors, the product obtained by said method has been found to have a Z configuration and is not a substituted diene carboxylic acid ester having an E configuration.

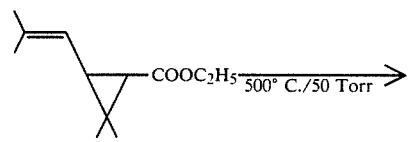

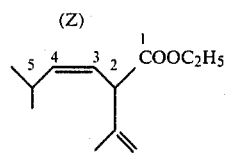

Also there has been known a method wherein an alkyl ester of substituted diene carboxylic acid is obtained by the dehydration and ring cleavage of an alkyl ester of trans-2,2-dimethyl-1-3-(1-hydroxy-2-methylpropyl)cyclopropane-1-carboxylic acid [Japanese published examined patent publication No. 19056/1966, Agr. Biol. Chem., 28, 456 (1964) and Tetrahedron Letters, 2441 (1976)]. However, in this case, the raw material thereof has to be synthesized via many complicated processes starting from trans-caronic acid of isobutyric acid chloride; consequently, this method is not a satisfactory one when carried out in an industrial scale.

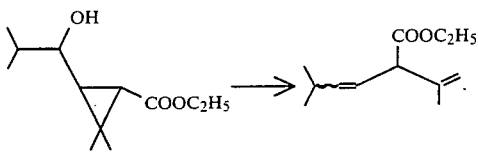

Further, it has been reported that, though it is different from the method of the present invention in that a carboxylic acid is used as the starting material, a diene carboxylic acid is obtained by heating trans-chrysanthemic acid together with pyridine hydrochloride up to 210° C. [J. Chem. Soc. Perkin Trans., I, 196(1977)]. According to this report, the main components of the product are olefin and lactones which are neutral substances, and the yield of substituted diene carboxylic acid is extremely low. Thus, the product can hardly be used as an intermediate aimed by the present invention.

Under such situations, the present inventors have investigated various method for the preparation of a substituted diene alcohol represented by the general formula (III) mentioned above, and found that, by the treatment of a chrisanthemic acid ester represented by the general formula (I) with Brönsted acid such as sulfonic acid or sulfuric acid, the ring cleavage of a cyclopropane compound selectively takes place at the 2,3-position, a substituted diene carboxylic acid ester having an E configuration represented by the general formula (II-a) can be obtained in a high yield, that a substituted diene alcohol having an E configuration represented by a general formula (III-a);

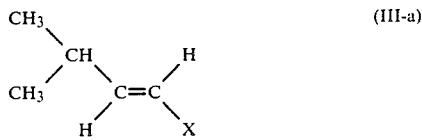

wherein X is the same as mentioned above can be obtained by the reduction of a lower alkoxycarbonyl group of said substituted diene carboxylic acid ester to methylol, and that a substituted diene alcohol having a Z configuration represented by a general formula (III-b):

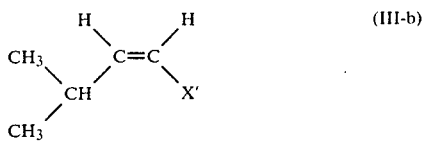

wherein X' represents a group represented by a formula

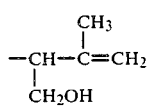

can be obtained also from a substituted diene carboxylic acid ester having a Z configuration represented by the general formula (II-b), which is obtained by the thermal cleavage of a chrysanthemic acid ester represented by the general formula (I) by the reduction of the lower alkoxycarbonyl group thereof. Thus, the present invention has been completed.

In the present invention, the chrysanthemic acid ester represented by the general formula (I), which is the starting material, may be of any of trans isomer, cis isomer or the mixture thereof. As the substituted group R thereof, there can be illustrated methyl group, ethyl group, propyl group, butyl group and the like.

In the reaction to obtain a substituted diene carboxylic acid ester represented by the general formula (II-a) by the treatment of said chrysanthemic acid ester with Brönsted acid mentioned above, as the Brönsted acid there are used, for example, aryl or alkyl sulfonic acids such as p-toluenesulfonic acid, benzenesulfonic acid, naphthalenesulfonic acid, methanesulfonic acid, trifluoromethanesulfonic acid and the like, and sulfuric acid. The amount to be used is usually in a range of 1/100 to equivalent mole, preferably 1/10 to ½ mole based upon 1 mole of the starting material chrysanthemic acid ester.

In the present invention, solvent is not always necessary. However, in order to make the reaction proceed more smoothly, it is preferable to use a solvent which does not substantially hinder the present reaction. As such solvents, there can be illustrated halogenated hydrocarbons such as chloroform and dichloroethane, aromatic hydrocarbons such as benzene and toluene, saturated hydrocarbons such as hexane and heptane and a mixed solvent of them.

The reaction temperature is usually in a range of 10° C. to 150° C. or the boiling point of the solvent used, preferably 20° C. to 150° C. Though the reaction time varies depending upon the reaction conditions, the object can be sufficiently accomplished within 10 minutes to 50 hours. The extent of the reaction progress can be confirmed with gas chromatgraphy or thin-layer chromatography.

Though the reaction can be carried out under any condition of reduced pressure to increased pressure, the object can be easily achieved under the atmospheric pressure.

When the present invention is carried out, any of the batch process or continuous process may be adopted. As the method to charge the starting material, there can be adopted any of the method wherein it is charged in the reactor together with the Brönsted acid at a time or one wherein it is charged to the reactor continuously or intermittently according to the extent of the reaction progress.

As mentioned above, after the reaction is completed, the Brönsted acid used is removed from the reaction mixture by such means as extraction, filtration or washing. Then, the reaction mixture is concentrated to obtain the substituted diene carboxylic acid ester aimed.

This product can be further refined by such means as distillation or chromatography, if necessary.

Also in the reaction to obtain a substituted diene carboxylic acid ester represented by the general formula (II-b) by the thermal cleavage of a chrysanthemic acid ester represented by the general formula (I) mentioned above, as the conditions for the thermal cleavage, the reaction can be effectively carried out under the atmospheric or reduced pressure at a temperature of from about 400° to 600° C.

As the style of the reaction, any of batch style and continuous style may be adopted. However, the style wherein a packing such as glass, alumina or silica is packed in a reaction tube and the starting material is allowed to pass through it while keeping the required temperature is industrially advantageous.

The thermal cleavage product thus obtained can be purified by distillation or chromatography, if necessary.

As the selective reducing agent of the alkoxycarbonyl group of the substituted diene carboxylic acid ester represented by the general formulas (II-a) and (II-b), which is obtained by the procedure as mentioned above, to obtain a substituted diene alcohol, there can be illustrated such ones as aluminum hydride compounds and boron hydride compounds.

As aluminum hydride compounds, there can be illustrated lithium aluminum hydride, lithium ethoxyaluminum hydride, sodium aluminum hydride, sodium bis(2-methoxy-ethoxy)aluminum hydride, alane and the like.

Also as boron hydride compounds, there can be, for example, illustrated lithium borohydride, lithium triethylborohydride, lithium tri-sec-butylborohydride and the like.

In this case, it is preferable to carry out the reaction in an inert solvent such as diethyl ether, tetrahydrofuran, dimethoxyethane or diglyme. Also an aromatic hydrocarbon such as benzene or toluene may be used together with it.

There is no particular limitation on the reaction temperature. The reaction may be freely carried out in a range from $-78°$ C. to the boiling point of the solvent.

After conducting the reduction as mentioned above, the reaction mixture is treated with an aqueous solution of a mineral acid such as diluted hydrochloric acid or an aqueous solution of an alkali such as sodium hydroxide and then extracted by an organic solvent whereby the aimed product, substituted diene alcohol, can be obtained.

Though the substituted diene alcohol thus obtained has a high purity in itself, it can be further refined by such means as distillation or chromatography, if necessary.

The present invention provides also the method for the preparation of a substituted alcohol represented by a formula (V):

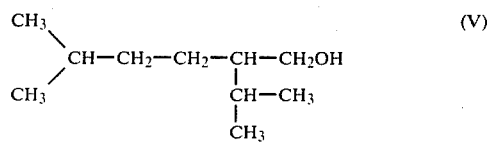

by conducting the hydrogenation of the substituted diene alcohol represented by the general formula (III) or by conducting the hydrogenation of the substituted diene carboxylic acid ester represented by a formula (II-a) or (II-b) followed by the reduction of lower alkoxycarbonyl group thereof.

The substituted alcohol represented by the formula (V) mentioned above is called tetrahydrolavandulol. It is compound usable as a perfume.

In the method for the preparation of the substituted alcohol represented by the formula (V), as the catalyst used for the addition of hydrogen to the double bond of the substituted diene alcohol represented by the general formula (III), there can be illustrated catalysts such as nickel, palladium, platinum or oxides of elements mentioned above and supported ones on a suitable support; and as the support, there are used activated carbon, alumina and the like.

In this case, the pressure of hydrogen is usually from atmospheric pressure to 100 atms. There is no particular limitation on the solvent as far as it does not give any unfavorable effects to the reaction and it is preferable to use a lower alcohol such as methanol or ethanol. Usually, the reaction temperature may be optionally decided within a range of $0°$ C. to the boiling point of the solvent to be used.

After conducting the catalytic reduction as mentioned above, the catalyst is removed by filtration or other means and the reaction solution is concentrated whereby the substituted alcohol represented by the general formula (V) mentioned above can be obtained.

Also a substituted diene carboxylic acid ester represented by the general formula (II-a) or (II-b) is subjected to the hydrogenation as mentioned above to be led to a substituted carboxylic acid ester represented by a general formula (IV):

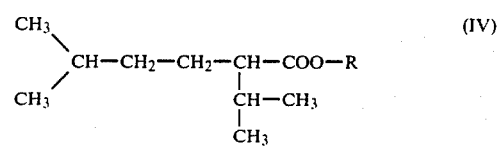

wherein R is the same as that mentioned above and then the lower alkoxycarbonyl group of said ester is reduced in the same manner as that mentioned above whereby a substituted alcohol represented by the formula (V) can be obtained.

In addition, each product obtained as mentioned above has a high purity in itself. However, also it can be further refined by such means as distillation or chromatography, if necessary.

When an optically active chrysanthemic acid ester is used as the starting material, the substituted diene carboxylic acid ester, substituted diene alcohol and tetrahydrolavandulol are obtained in their optically active form.

The present invention mentioned above can be diagramatically shown as follows:

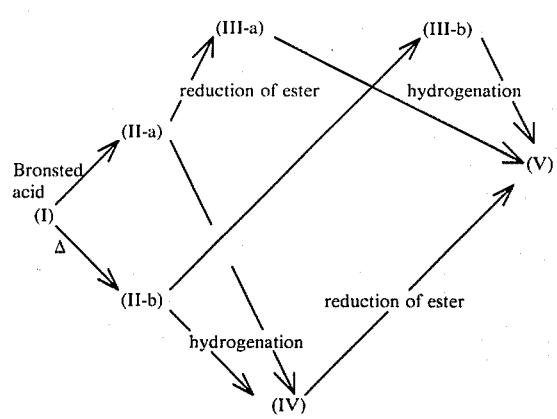

Further the present invention will be described with examples as below.

EXAMPLE 1

In a 1-l flask, there were charged 20.0 g of chrysanthemic acid ethyl ester (cis/trans±35/65) and 400 ml of toluene, and 5.0 g of p-toluenesulfonic acid was added thereto. The mixture was stirred at 110° C. for 6 hours. After cooling the reaction mixture, the mixture was washed with water and concentrated to give 15.2 g of the residue. Then, it was distilled (b.p.: 50°–75° C./1.5 mmHg) to give 12.8 g of light yellow oil. This oil was, according to the gas chromatographic analysis thereof, composed of two main components the ratio of which was 49.4% of the compound (1) and 50.6% of the compound (2), respectively.

Then, 10 g of this distillate was rectified to give 4.0 g of a fraction having a boiling point of 98°–100° C./11 mmHg (content of the compound (1): 95.5%) and 4.1 g of a fraction having a boiling point of 71°–73° C./1.2 mmHg (content of the compound (2): 95.6%).

Based on the spectrum data mentioned below, it was confirmed that compound (1): ethyl (E)-5-methyl-2-(1-methylethenyl)-3-hexenoate
compound (2): ethyl (E)-5-methyl-2-(1-methylethylidene)-3-hexenoate.

compound (1)

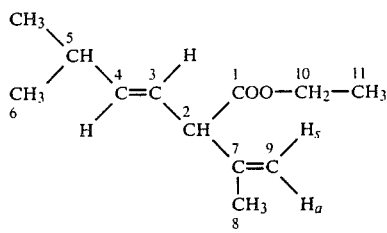

IR spectrum (NaCl, liquid film). $\nu cm^{-1}$: 1740, 1650, 900.

NMR spectrum (CDCl$_3$, TMS, 200 MHz). δ(ppm): 5.54 (H-3, H-4, m); 4.87 (H-9, a, s, s); 4.15 (H-10, q, $J_{10,11}$=6.8 Hz); 3.60 (H-2, d, $J_{2,3}$=6.8 Hz); 2.36 (H-5, m); 1.76 (H-8, s); 1.26 (H-11, t, $J_{10,11}$=6.8 Hz); 1.00 (H-6, d, $J_{5,6}$=6.8 Hz).

It was confirmed that the configuration of H-3 and H-4 was E-form from the 60 MHz NMR spectrum ($J_{3,4}$=15.7 Hz) obtained using Eu (fod)$_3$ as the shift reagent.

compound (2)

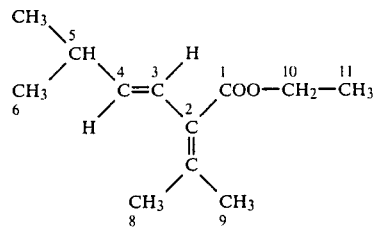

(IR spectrum (NaCl, liquid film). $\nu cm^{-1}$: 1735, 1650, 1640, 970.

NMR spectrum (CDCl$_3$, TMS, 60 MHz). δ(ppm): 6.2 (H-3, d, $J_{3,4}$=17 Hz); 5,45 (H-4, q, $J_{3,4}$=17 Hz, $J_{4,5}$=7 Hz); 4.25 (H-10, q, $J_{10,11}$=7 Hz); 2.2 (H-5, m); 1.8 (H-8, H-9, s); 1.3 (H-11, t, $J_{10,11}$=7 Hz); 0.95 (H-6, d, $J_{5,6}$=6 Hz).

It was confirmed that the configuration of H-3 and H-4 was E-form from the coupling constant between H-3 and H-4 ($J_{3,4}$=17 Hz).

EXAMPLE 2

In a 50 ml flask, there was charged 4.1 g of chrysanthemic acid ethyl ester (cis/trans=35/65) and 10 ml of toluene, and 2.1 g of 2-naphthalenesulfonic acid was added thereto. The mixture was stirred at 110° C. for 5 hours. Then the reaction mixture was treated as in Example 1. After the concentration and distillation, there was obtained 1.96 g of a fraction having a boiling point of 60°–71° C./1.0 mmHg.

This substance had, according to the gas chromatographic analysis thereof, a composition of 4.3% of the compound (1), 81.4% of the compound (2) mentioned above, respectively, and 14.3% of the starting material.

EXAMPLE 3

In a 100 ml flask, there were charged 2.5 g of chrysanthemic acid ethyl ester (cis/trans=99/1) and 47.5 g of 1,2-dichloroethane. To this mixture was added 0.31 g of concentrated sulfuric acid follwed by stirring at 70° C. for 1 hour. After cooling of the reaction mixture, the mixture was washed with water and concentrated to give 2.3 of the residue. Then, it was distilled (b.p.: 50°–75° C./1.5 mmHg) to obtain 1.9 g of a light yellow oil. This oil had, according to the gas chromatographic analysis thereof, a composition of 52.2% of the compound (1), 22.3% of the compound (2) mentioned above, respectively, and 15.7% of the starting material.

EXAMPLE 4

In a 100 ml flask, there were charged 2.5 g of chrysanthemic acid ethyl ester and 47.5 g of 1,2-dichloroethane. To this mixture was added 0.19 g of trifluoromethanesulfonic acid and the mixture was stirred at 21° C. for 26 hours. After the reaction mixture was washed with water and concentrated to give 2.4 g of the residue. Then, it was distilled (b.p.: 52°–75° C./1.5 mmHg) to give 2.2 g of light yellow oil. This oil had, according to the gas chromatographic analysis, a composition of 58.5% of the compound (1), 18.9% of the compound (2) mentioned above, respectively, and 21.9% of the raw material.

EXAMPLE 5

In a 500 ml flask, there were charged 10.0 g of (1R)-chrysanthemic acid ethyl ester (cis/trans=19/81) and 190.0 g of dichloroethane. To this mixture was added 1.8 g of methanesulfonic acid followed by stirring at 70° C. for 2 hours. After cooling of the reaction mixture, the mixture was washed with water and concentrated. The residue was distilled in vacuo to give 9.12 g of the distillate at the boiling point of 52°–74° C./1.5 mmHg. This distillate had, according to the gas chromatographic analysis, a composition of 40.2% of the compound (1), 39.0% of the compound (2) mentioned above, respectively, and the starting material (cis-form: 0.5% and trans-form: 14.8%).

Then, 8.95 g of this distillate was rectified to give 2.9 g of the optically active compound (1) having the boiling point of 99°–101° C./16 mmHg. This substance had an optical rotation of $\alpha_D^{20.5}=-18.04°$ (neat) and it was found that this substance was ethyl 1-(E)-5-methyl-2-(1-methylethenyl)-3-hexenoate, namely the optically active compound (1) mentioned above having a chemical purity of 97.5% by the gas chromatographyic analysis.

EXAMPLE 6

In a 500 ml flask, there were charged 2.61 g of lithium aluminum hydride and 100 ml of dry ether under nitrogen atmosphere. While stirring the mixture at −20° C., a solution of 17.9 g of (E)-5-methyl-2-(1-methyl-ethenyl)-3-hexenoic acid ethyl ester in 100 ml of dry ether was added dropwise to the mixture. Then, the mixture was stirred at −20° C. for 1 hour. The reaction mixture was gradually poured into an ice water under nitrogen atmosphere and the solution was made acidic with dilute hydrochloric acid. After the ether layer was separated, the water layer was extracted with ether. The ether layer was combined with the ether layer obtained above. The combined ether layer was concentrated to give 14.4 g of light yellow oil. Then, it was distilled to obtain 12.9 g of oil (b.p.: 75°-77° C./6 mmHg).

Based on the spectrum data mentioned below, it was confirmed that said distillate was (E)-5-methyl-2-(1-methyl-ethenyl)-3-hexene-1-ol.

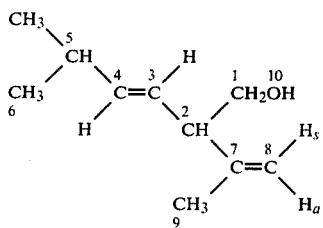

IR spectrum (NaCl, liquid film). $\nu cm^{-1}$: 3360, 3080, 1640, 980, 900.

NMR spectrum (CCl$_4$, TMS, 200 MHz). δ(ppm): 5.54 (H-3, dd, $J_{3,4}=15.1$ Hz, $J_{2,3}=6.3$ Hz); 5.26 (H-4, dd, $J_{3,4}=15.1$ Hz, $J_{4,5}=8.3$ Hz); 4.87 (H-8s, s); 4.78 (H-8a, s); 3.58 (H-1, m); 2.83 (H-2, m); 2.28 (H-5, m); 1.77 (H-10, s); 1.72 (H-9, s); 0.99 (H-6, d, $J_{5,6}=6.8$ Hz).

It was confirmed that the configuration of H-3 and H-4 was E-form from the coupling constant between H-3 and H-4 ($J_{3,4}=15.1$ Hz).

EXAMPLE 7

In a 25 ml flask, there were charged 0.8 g of lithium aluminum hydride and 10 ml of dry ether under the nitrogen atmosphere, and the mixture was cooled to −25° C. while stirring. To the mixture was added dropwise 0.5 g of optically active compound (1), which was obtained in Example 5, in 5 ml dry ether followed by stirring at the same temperature for 1 hour.

Then the reaction mixture was poured into ice- water gradually under nitrogen atmosphere while stirring followed by separating into the organic layer and the aqueous layer. The aqueous layer was extracted with ether and the organic layer was combined with one obtained above. The organic layer was washed with water and dried with anhydrous sodium sulfate, followed by the concentration in vacuo to give 0.4 g of oil.

And then the oil was distilled in vacuo to give 0.37 g of colorless oil (b.p.: 130°-135° C./21 mmHg).

Its IR and NMR spectra were identical with those of (E)-5-methyl-2-(1-methyl-ethenyl)-3-hexene-1-ol obtained in Example 6, its chemical purity was 97.5% by the gas chromatographic analysis and its optical rotation was $\alpha_D^{24}$ −35.9° (neat). Based on the data mentioned above, it was confirmed that the product was optically active 1-(E)-5-methyl-2-(1-methyl-ethenyl)-3-hexene-1-ol.

EXAMPLE 8

In a 500 ml flask, 6.61 g of lithium aluminum hydride was suspended in 200 ml of dry ether under nitrogen atmosphere. To this suspension was added dropwise a mixture solution consisting of 8.02 g of dry ethanol and 50 ml of dry ether. Then, the mixture was stirred at 0° C. for 1 hour, followed by cooling to −20° C. To this solution was added dropwise a solution of 24.9 g of (E)-5-methyl-2-(1-methyl-ethylidene)-3-hexenoic acid ethyl ester in 75 ml of dry ether. After the addition was completed, the mixture was stirred at −20° C. for 7 hours. Then, it was subjected to the same post-treatment as that in Example 6 to give 17.5 g of light yellow oil. This was distilled to give 12.9 g of oil (b.p.: 72° C./2 mmHg–73° C./1 mmHg). Based on the spectrum data mentioned below, it was confirmed that this substance was (E)-5-methyl-2-(1-methyl-ethylidene)-3-hexene-1-ol.

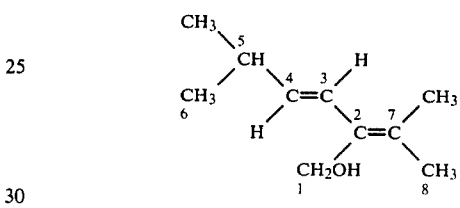

IR spectrum (NaCl, liquid film). $\nu cm^{-1}$: 3450, 1382, 1160, 1020.

NMR spectrum (CCl$_4$, TMS, 60 MHz). δ(ppm): 6.23 (H-3, d, $J_{3,4}=16$ Hz); 5.65 (H-4, dd, $J_{3,4}=16$ Hz, $J_{4,5}=6.5$ Hz); 4.17 (H-1, s); 2.57 (H-9, s); 2.3 (H-5, m); 1.83 (H-8, s); 1.80 (H-8, s); 1.0 (H-6, d, $J_{5,6}=7$ Hz).

EXAMPLE 9

Small pieces of quartz were packed in a quartz tube (outside diameter: 18 mm, inside diameter: 15 mm, length: 400 mm) and the tube was heated up to 500° C. in an oven. A dry ice trap was attached to the outlet of the reactor in order to collect the product.

In the nitrogen gas flow, 53.3 g of chrystanthemic acid ethyl ester was put dropwise (S.V.=184/min., ester/N$_2$=¼) into the quartz tube to be subjected the thermal cleavage to give 46.5 g of a light yellow oil. The composition of this oil was analyzed by gas chromatography. As the result, it was found that ethyl (Z)-2-isopropenyl-5-methyl-3-hexenoate was 68%, the starting material was 22% and low boiling component was 10%.

Then, this product was rectified to give ethyl (Z)-2-isopropenyl-5-methyl-3-hexenoate (b.p.: 91° C./10 mmHg).

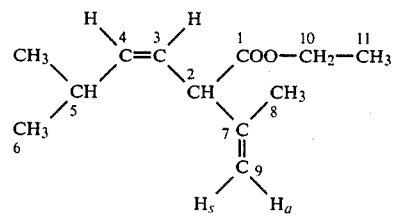

NMR spectrum (CDCl$_3$, TMS, 200 MHz). δ(ppm): 5.52 (H-3, t, $J_{2,3}=J_{3,4}=9.3$ Hz); 5.42 (H-4, t, $J_{3,4}=J_{4,5}=9.3$ Hz); 4.91 (H-9s, s); 4.89 (H-9a, s); 4.16 (H-10, q, $J_{10,11}=7.3$ Hz); 4.00 (H-2, d, $J_{2,3}=9.3$ Hz); 2.6 (H-5, m); 1.78 (H-8, s); 1.26 (H-11, t, $J_{10,11}=7.3$ Hz); 0.97, 0.95 (H-6, d, $J_{5,6}=5.4$ Hz).

IR specrrum (NaCl, liquid film). $\nu cm^{-1}$: 2960, 1740, 1645, 1040, 900.

It was confirmed that the configuration of H-3 and H-4 was Z-form from the coupling constant between H-3 and H-4 ($J_{3,4}=9.3$ Hz).

EXAMPLE 10

Under nitrogen atmosphere, 2.92 g (77 millimole) of lithium aluminum hydride and 150 ml of dry ether wee charged in a 300 ml three necked flask. Then, the mixture was cooled to $-25°$ C. and, while stirring, a solution of 20.1 g (102 millimole) of ethyl (Z)-2-isopropenyl-5-methyl-3-hexenoate in 50 ml of dry ether was added dropwise over 2 hours. After the addition was completed, the stirring was further continued at $-25°$ C. for 2 hours so that the reaction was completed. Then, the reaction mixture was subjected to the usual post-treatment followed by the ether extraction. The ether layer was concentrated to give 15.42 g of a light yellow oil.

Then, it was distilled (b.p.: 63°-64° C./2.5 mmHg) to give 13.98 g of (Z)-2-isopropenyl-5-methyl-3-hexene-1-ol as a colorless oil (yield: 89%).

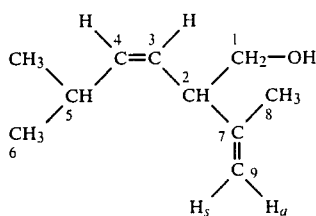

IR spectrum (NaCl, liquid film). $\nu cm^{-1}$: 3360, 2960, 1645, 1470, 1380, 1050, 895.

NMR spectrum (CDCl$_3$, TMS, 200 MHz). δ(ppm): 5.39 (H-3, t, $J_{2,3}=J_{3,4}=10.3$ Hz); 5.13 (H-4, t, $J_{3,4}=J_{4,5}=10.3$ Hz); 4.86 (H-9s, s); 4.80 (H-9a, s); 3.6 (H-1, m); 3.3 (H-2, m); 2.7 (H-5, m); 1.95 (—OH, bs); 1.73 (H-8, s); 0.97, 0.95 (H-6, d, $J_{5,6}=6.8$ Hz).

It was confirmed that the configuration of H-3 and H-4 was Z-form from the coupling constant between H-3 and H-4 ($J_{3,4}=10.3$ Hz).

EXAMPLE 11

In a 50 ml flask, 0.2 g of 5% palladium-carbon was suspended in 5 ml of dry ethanol at the room temperature under nitrogen atmosphere.

Into the mixture was added 2.0 g of (E)-5-methyl-2-(1-methyl-ethenyl)-3-hexene-1-ol, followed by stirring vigorously under hydrogen atmosphere at the room temperature. At the time when hydrogen uptake was 650 ml, the reaction was stopped. After the catalyst was filtered off, the filtrate was concentrated to give 1.8 g of light yellow oil. Then, this was distilled to give 1.5 g of a fraction at the boiling point of 71°-73° C./4 mmHg.

Based on the spectrum data mentioned below, it was confirmed that this oil was 2-isopropyl-5-methyl-hexane-1-ol.

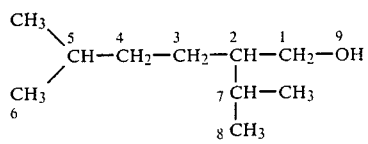

IR spectrum (NaCl, liquid film). $\nu cm^{-1}$: 3330, 1460, 1380, 1365, 1050.

NMR spectrum (CCl$_4$, TMS, 60 MHz). δ(ppm): 3.43 (H-1, d); 3.07 (H-9, br); 2.1-0.6 (H-2, 3, 4, 5, 7, m); 0.87 (H-6, 8, d, $J_{5,6}=J_{7,8}=6$ Hz).

EXAMPLE 12

The catalytic reduction was conducted in accordance with the same procedure as that in Example 11 except that 2.0 g of (E)-5-methyl-2-(1-methyl-ethylidene)-3-hexene-1-ol was used in place of (E)-5-methyl-2-(1-methyl-ethenyl)-3-hexene-1-ol in Example 11. At the time when hydrogen uptake was 650 ml, the reaction was stopped. After that, the same procedure as mentioned above was conducted to obtain 1.63 g of a light yellow oil as the residue. This oil was further distilled to give 1.4 g of a fraction at the boiling point of 71°-73° C./4 mmHg.

Its IR and NMR spectra were identical with those of 2-isopropyl-5-methyl-hexane-1-ol obtained in Example 11 mentioned above.

EXAMPLE 13

Under nitrogen atmosphere, 1.5 g of 5% palladium-carbon was suspended in 100 ml of dry ethanol at the room temperature, and 20.0 g of (E)-5-methyl-2-(1-methylethenyl)-3-hexenoic acid ethyl ester was added thereto. Then, under hydrogen atmosphere, the mixture was vigorously stirred at the room temperature for 7 hours. At the time when about 5.2 liter of hydrogen gas was absorbed, the reaction was stopped. After the catalyst was filtered off, the filtrate was concentrated to give 17.5 g of a light yellow oil. Then, it was distilled to give 16.3 g of oil (b.p.: 67°-71° C./5 mmHg). Based on the spectrum data mentioned below, it was confirmed that this substance was 2-isopropyl-5-methyl-hexanoic acid ethyl ester.

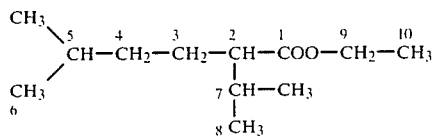

NMR spectrum (CCl$_4$, TMS, 60 MHz). δ(ppm): 4.05 (H-9, q, $J_{9,10}=7$ Hz); 2.1-0.7 (H-2, 3, 4, 5, 7, m); 1.25 (H-10, t, $J_{9,10}=7$ Hz); 0.85 (H-6, H-8, d, $J_{5,6}=J_{7,8}=5.5$ Hz).

Then, said ester was treated with 1.95 g of lithium aluminum hydride and 210 ml of dry ether in the same manner as that in Example 6 to give 13.1 g of a light yellow oil. Then, it was distilled to give 10.5 g of a fraction at the boiling point of 72°-73° C./4 mmHg as an oily substance.

The IR and NMR spectra of this substance were identical with those of 2-isopropyl-5-methyl-hexane-1-ol obtained in Example 11.

EXAMPLE 14

Into a flask 0.6 g of platinum oxide and 3 ml of ethanol were charged under nitrogen atmosphere. After the gas in the flask was replaced with hydrogen gas, the reaction mixture was stirred vigorously in the same atmosphere at the room temperature. After 30 minutes, 0.5 g of the optically active compound (1) obtained in Example 5 was added dropwise thereto and the mixture was vigorously stirred until the absorption of hydrogen was ceased. After the catalyst was filtered off, the filtrate was concentrated under a reduced pressure and distilled to give 0.44 g of oil (b.p.: 65°–75° C./5 mmHg). This oil was ethyl d-2-isopropyl-5-methyl-hexanoate having an optical rotation of $\alpha_D^{21} = +9.27°$ (neat) and the NMR spectrum thereof was identical with that in Example 13.

A part of this substance was hydrolyzed to the corresponding carboxylic acid, which was esterified with an optical active alcohol mentioned below to synthesize a diastereomeric ester for determining the ratio of optical isomers of said carboxylic acid. The results were shown as below.

| Diastereomeric ester | Ratio of optical isomers |
| --- | --- |
| d-2-octyl ester | 97.6%:2.4% |
| l-menthyl ester | 97.1%:2.9% |

EXAMPLE 15

After 100 ml of ethanol, 1.5 g of 5% palladium-carbon and 20 g of ethyl (Z)-2-isopropenyl-5-methyl-3-hexenoate were charged into a 200 ml three necked flask, hydrogen gas was introduced into the flask, and the mixture was stirred under the atmospheric pressure. At the time point when the absorption of hydrogen was ceased, the reaction was stopped. After the catalyst was filtered off, the filtrate was concentrated to give 17.5 g of oil.

Then, it was dissolved in 150 ml of dry ether. This solution was added dropwise into a 500 ml flask where 2.35 g of lithium aluminum hydride and 150 ml of dry ether were charged. The procedure was conducted at −20° C. under nitrogen atmosphere while stirring. After the addition was completed, the stirring was further continued at −20° C. for 1 hour followed by the usual post-treatment. The crude product obtained was distilled (b.p.: 73° C./4 mmHg) to give 13.1 g of colorless oil (yield: 81%).

The IR and NMR of this oil were identical with those of 2-isopropyl-5-methyl-hexane-1-ol obtained in Example 11.

EXAMPLE 16

Into a 25 ml flask wherein 0.2 g of lithium aluminum hydride and 3 ml of dry ether were charged under nitrogen atmosphere, followed by stirring at −30° C., and thereinto was added dropwise a solution containing 0.42 g of ethyl d-2-isopropyl-5-methyl-hexanoate obtained in Example 14 and 2 ml of dry ether. After stirring at −30°–−10° C. for 3 hours, ethyl acetate was added to the reaction mixture and the mixture was poured into an ice water, followed by separating into the organic layer and the aqueous layer. The organic layer was washed with a dilute hydrochloric acid solution, a dilute alkaline solution and then water, and dried over anhydrous sodium sulfate. After concentration, the residue was distilled to give 0.32 g of a distillate at the boiling point of 130°–135° C./20 mmHg. The optical rotation of this substance was $\alpha_D^{20} = +12.89°$ (neat). Based on the spectrum data mentioned below, it was confirmed that this substance was d-tetrahydrolavandulol.

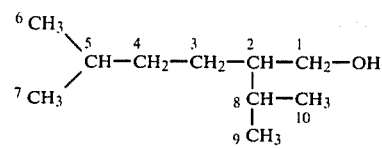

NMR spectrum $C^{13}$ (22.5 MHz, CDCl$_3$). δ(ppm): 63.8 (t, C-1); 47.0 (d, C-2); 37.2 (t, C-3 or 4); 28.5 (d, C-8); 28.0 (d, C-5); 25.5 (t, C-4 or 3); 22.8 (q, C-6 or 7 or 9 or 10); 22.5 (q, C-6 or 7 or 9 or 10); 19.8 (q, C-6 or 7 or 9 or 10); 19.3 (q, C-6 or 7 or 9 or 10).

$H^1$ (90 MHz, CDCl$_3$). δ(ppm): 3.55 (m, H-1); near 1.7 (bm, H-5, H-8, H-2); 1.62 (b.s., OH); 1.25 (m, H-3, H-4); 0.89 (d, H-6, 7, 9, 10).

We claim:

1. A process for the preparation of a substituted diene carboxylic acid ester having an E configuration represented by the formula:

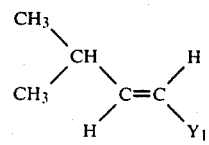

wherein $Y_1$ represents a group of the formula

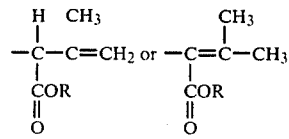

wherein R represents a lower alkyl group which comprises conducting the treatment of a chrysanthemic acid ester represented by the formula:

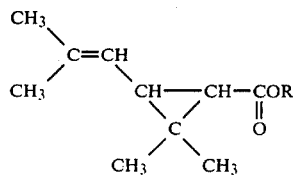

wherein R represents the same as that mentioned above, with sulfonic acid or sulfuric acid.

2. The process as claimed in claim 1 wherein, as the sulfonic acid, aryl sulfonic acid or alkyl sulfonic acid is used.

3. The process as claimed in claim 2 wherein, as the aryl sulfonic acid, p-toluenesulfonic acid, benzenesulfonic acid or naphthalenesulfonic acid is used.

4. The process as claimed in claim 2 wherein, as the alkyl sulfonic acid, methanesulfonic acid or trifluoromethanesulfonic acid is used.

5. The process as claimed in claim 1, wherein 1/100 mole to equivalent mole of the sulfonic acid or sulfuric acid is used based on 1 mole of the chrysanthemic acid ester.

6. The process as claimed in claim 1 wherein, as the solvent, halogenated hydrocarbon, aromatic hydrocarbon or saturated hydrocarbon, or a mixed solvent thereof is used.

7. The process as claimed in claim 1 wherein the reaction is conducted at a temperature of from 10° C. to 150° C. or the boiling point of the solvent used.

8. The process of claim 2 wherein 1/100 to one equivalent mole of the sulfonic acid or sulfuric acid is used based on 1 mole of the chrysanthemic acid ester.

9. The process of claim 3 wherein 1/100 to one equivalent mole of the sulfonic acid or sulfuric acid is used based on 1 mole of the chrysanthemic acid ester.

10. The process of claim 4 wherein 1/100 to one equivalent mole of the sulfonic acid or sulfuric acid is used based on 1 mole of the chrysanthemic acid ester.

* * * * *